United States Patent
Propp

(12) 
(10) Patent No.: US 7,232,427 B2
(45) Date of Patent: Jun. 19, 2007

(54) JUGULAR AND SUBCLAVIAN ACCESS SITE DRESSING, ANCHORING SYSTEM AND METHOD

(75) Inventor: Donald J. Propp, Dewitt, MI (US)

(73) Assignee: Tri-State Hospital Supply Corporation, Howell, MI (US)

( * ) Notice: Subject to any disclaimer, the term of this patent is extended or adjusted under 35 U.S.C. 154(b) by 151 days.

(21) Appl. No.: 10/866,983

(22) Filed: Jun. 14, 2004

(65) Prior Publication Data

US 2005/0277888 A1 Dec. 15, 2005

(51) Int. Cl.
*A61M 5/32* (2006.01)
(52) U.S. Cl. ...................... 604/180; 128/849
(58) Field of Classification Search ........ 604/174–175, 604/180, 304–305, 307; 128/DIG. 6, DIG. 26, 128/898, 849
See application file for complete search history.

(56) References Cited

U.S. PATENT DOCUMENTS

| | | | | |
|---|---|---|---|---|
| 3,046,984 A | * | 7/1962 | Eby | 604/180 |
| 4,324,237 A | * | 4/1982 | Buttaravoli | 602/54 |
| 4,485,809 A | * | 12/1984 | Dellas | 602/52 |
| 4,669,458 A | * | 6/1987 | Abraham et al. | 128/846 |
| 4,759,354 A | * | 7/1988 | Quarfoot | 602/50 |
| 5,342,317 A | * | 8/1994 | Claywell | 604/179 |
| 5,354,282 A | * | 10/1994 | Bierman | 604/180 |
| 5,605,546 A | * | 2/1997 | Wolzinger et al. | 604/174 |
| 5,916,199 A | * | 6/1999 | Miles | 604/174 |
| 6,626,884 B1 | * | 9/2003 | Dillon et al. | 604/409 |

* cited by examiner

*Primary Examiner*—Nicholas Lucchesi
*Assistant Examiner*—Theodore J. Stigell
(74) *Attorney, Agent, or Firm*—Fildes & Outland, P.C.

(57) ABSTRACT

A system adapted to tend a jugular or subclavian catheter and connecting tubing includes a jugular and subclavian access site dressing and a medical tubing anchor. The dressing is adapted to protect and cover a catheter access site and the catheter. The medical tubing anchor is spacedly disposed from the dressing. The connecting tubing connects with the catheter and the system allows for movement of the tubing without the tubing exerting a pulling force on the catheter.

3 Claims, 2 Drawing Sheets

JUGULAR AND SUBCLAVIAN ACCESS SITE DRESSING, ANCHORING SYSTEM AND METHOD

TECHNICAL FIELD

This invention relates to dermal dressings and medical tubing anchors for the protection of jugular or subclavian catheter access sites, and more particularly to a system for protecting, anchoring, and securing introducer sheaths and catheters at and around a jugular or subclavian access site.

BACKGROUND OF THE INVENTION

It is known in the art relating to jugular and subclavian access site dressings used during and shortly after medical procedures such as open heart or thoracic surgery that the dressings have a tendency to become dislodged from the patient's skin, thereby exposing the access site to harmful bacteria and other pathogens. Some common forms of traditional access site dressings include self-adherent protective bandage tape or clear film product alternatives that use non-sensitizing hypoallergenic adhesives to cover all or part of the indwelling catheter access site. Some dressings also combine non-woven tape and absorbent gauze-like materials which have skin-mating surfaces of non-adherent film to reduce the effect of adhesive stripping caused by the dressing removal. One known dressing system includes an opaque pad for adhesive placement over an access site and an adhesive strip, for adhesive securement to the skin of a patient under a catheter tube as it emerges from underneath the pad, and between the skin and the pad along the edges of the pad in opposite directions from the tube exit location. A known transparent type dressing includes a transparent film that does not adhere to the wound site to be viewed. This transparent dressing allows for the placement of a gauze or other absorbent material beneath the transparent film layer over the wound in order to provide absorbency thereby defeating the ability to view the wound site.

Further, in known prior art access site dressings, the side arm of an introducer sheath, which is at a 60 or 90 degree angle to the introducer sheath secured by the dressing, and other medical tubing and connectors, and stresses imparted thereto, can cause separation of the dressing from a patient's skin. When a patient moves his or her head, the side arm acts as a lever and tears loose the dressing. This is undesirable because a patient will often move his or her head and the dressing is ineffective if it releases from the patient's skin. Also, the side arm tends not to stay flat against a patient's body but instead projects or lifts up off the body, which further loosens the dressing. Even more, other medical tubing located at the access site, such as central venous catheters (CVC's), often dangle insecurely from the jugular access site. When this tubing gets caught on other objects, such as medical instruments or medical personnel's clothing, the force of the tubing catching also can tear the dressing from the access site.

Further, known prior art access site dressings have not been able to accommodate all of the potential combinations of medical tubing that can exist at a jugular access site. For example, during open heart and/or thoracic surgery, a jugular access site may accommodate an introducer sheath alone or an introducer sheath along with either a single, double, or triple lumen central venous catheters (CVC's). Alternatively, there may be an introducer sheath in combination with a pulmonary artery catheter (PAC) (for example a Swan-Ganz or similar) or an introducer sheath in combination with a Swan-Ganz catheter along with either a single, double, or triple lumen CVC's. Finally, after surgery in the operating room, the introducer sheath is usually removed within one to two days, but the CVC (either single, double, or triple lumen) may remain in the access site for up to seven or more days. The prior art dressings have been able to accommodate some of these combinations but no prior art dressing has been suitable for use with all of these possible combinations. Even those which do accommodate a few combinations often come loose from the skin within a day or less, and thus serve no useful clinical purpose.

Moreover, for medical procedures involving the jugular or subclavian access site, either a right side or a left side access site may be used. It is preferable to use the right side access site, but in approximately 40% of the cases, it is necessary to use the left side access site. Prior art access site dressings are capable of being used on either the right hand side or the left hand side, however, they do not secure and protect the catheters and access sites, and come loose prematurely on either the left or right side.

Furthermore, prior jugular and subclavian access site systems have not been able to suitably anchor the medical tubing that leads up to the access site. As previously mentioned, this is problematic for the reason that this tubing tends to dangle from the patient and can be pulled if caught on other objects or people. This not only puts a tearing pressure on the jugular access site dressing, but also can pull the medical tubing away from the access point on the patient's skin. Another shortcoming of prior anchoring methods used in jugular access site systems is that the tubing anchors are not designed in a way to clear the gown of the patient worn by the patient during and after the operating procedure. Most of these anchor devices have a low vertical profile (i.e., vertical height). This results in the tubing being anchored close to the patient's body. When a patient is wearing a hospital gown, the gown interferes with the tubing and/or the anchoring device used to anchor the tubing located at the jugular access site. Finally, prior medical tubing anchors are not able to anchor more than one tube at a time. Surgical procedures such as open heart surgery require multiple medical tubes at the jugular access site. Hence, multiple prior art anchors must be used to secure the medical tubing leading up to the jugular access site.

SUMMARY OF THE INVENTION

The present invention provides a system adapted to tend a jugular or subclavian catheter and connecting/medical tubing that prevents the catheter(s) and dressing from inadvertent release from a patient's body. The system isolates a portion the connecting/medical tubing, thereby negating the forces that cause the dressing to tear away from the skin. The present invention also provides a system that can accommodate the various sizes and combinations of medical tubing and catheters utilized at a catheter access site. This tubing may include an introducer sheath with a side arm, an introducer sheath with a side arm in combination with a pulmonary artery catheter, and either a single, double, or triple lumen CVC. Moreover, the system can be used on either a right-hand side or a left-hand side access site.

More particularly, the present invention provides an access site system that includes a dressing and a medical tubing anchor. The dressing may be a non-window or window dressing. Further, the connecting/medical tubes are arranged at and between the dressing and the medical tubing anchor in such a way as to eliminate the twisting and tearing forces exerted by the medical tubing. The dressing may wrap around the medical tubing, such as the side arm of an introducer sheath, to eliminate the tearing force caused by movement of the introducer sheath side arm. The medical tubing anchor eliminates the pulling force arising when dangling medical tubes catch on other objects or people's clothing by firmly anchoring the tubes. The present system may also provide for a strain relieving U-shaped bend in the medical tubing between the medical tubing anchor and the dressing. This stress relieving U-shaped bend flexes to and fro, up and down, left and right during any relative motion, in any direction between the anchor location and the catheter access site. It also eliminates the possibility of a tearing force arising at the dressing when a patient equipped with the present invention moves his or her head.

Specifically, a system adapted to tend a jugular or subclavian catheter and connecting tubing includes a dressing adapted to protect and cover a catheter access site and at least one catheter. The system further includes a medical tubing anchor including a base support adapted to mount to a patient's skin and a flexible anchor member on the base support adapted to receive and support the connecting tubing therein. The medical tubing anchor also includes a keeper on the anchor member for keeping tubing disposed in the anchor member from inadvertent release. The medical tubing anchor is spacedly disposed from the dressing. The connecting tubing connects with the catheter and the system, when rigged with adequate stress relieving tubing slack, allows for movement of the tubing without the tubing exerting a pulling force on the catheter.

In one embodiment, the catheter may be chosen from one of a group of single lumen central venous catheters, double lumen central venous catheters, triple lumen central venous catheters, and pulmonary artery catheters. The system may include a plurality of catheters. The connecting tubing may be received and supported by the tubing anchor such that at least a portion of the connecting tubing forms a U shape between the dressing and the tubing anchor. Alternatively, the connecting tubing may be received and supported by the tubing anchor such that the tubing is slack between the dressing and the tubing anchor. The dressing of the system may also include a closure member having an adhesive side and an opposite non-adhesive side, wherein the closure member is adapted to overlie and close an end of the layer member.

A method for protecting a jugular or subclavian access site of a patient and for securing medical tubing and catheters used during surgery such as open heart or thoracic surgery includes the step of providing a dressing adapted to protect and cover a catheter access site and at least one catheter. The dressing may be a non-window or a window dressing which includes a layer member having an opening therein bounded by an edge, and a transparent film layer adhered to a side of the layer member and closing the opening. The transparent film layer has an adhesive side and an opposite non-adhesive side. The method further includes the step of providing a medical tubing anchor. The medical tubing anchor includes a base support adapted to mount to a patient's skin and a flexible anchor member on the base support adapted to receive and support the connecting tubing therein. The medical tubing anchor also includes a keeper on the anchor member for keeping tubing disposed in the anchor member from inadvertent release.

In one embodiment, the method may further include the steps of: placing the adhesive side of the dressing onto an access site of a patient to secure medical tubing, to secure the catheter at the access site, and to protect the access site from contamination; inserting the medical tubing into the medical tubing anchor by squeezing and holding ends of the flexible anchor member and the base support to open tubing slots in the flexible anchor member; mounting the base support of the tubing anchor onto the skin of the patient on a side of the patient's body where the dressing is located such that the tubing anchor is spacedly disposed from the dressing; adjusting the medical tubing by squeezing and holding ends of the flexible anchor member and the base support of the medical tubing anchor to open the tubing slots so that the length of the medical tubing located between the dressing and the medical tubing anchor is greater than the distance between the access site and the medical tubing anchor, thereby causing the medical tubing to bend in a U shape between the dressing and the medical tubing anchor; and securing the medical tubing in the medical tubing anchor.

In an alternative embodiment, the method may further include the steps of: placing the adhesive side of the dressing onto an access site of a patient to secure medical tubing, to secure the catheter at the access site, and to protect the access site from contamination; mounting the base support of the tubing anchor onto the skin of the patient on a side of the patient's body where the dressing is located such that the tubing anchor is spacedly disposed from the dressing; after mounting the base support of the tubing anchor onto the skin, inserting the medical tubing into the medical tubing anchor by squeezing and holding ends of the flexible anchor member and the base support to open tubing slots in the flexible anchor member; after inserting the medical tubing into the medical tubing anchor, adjusting the medical tubing by squeezing and holding ends of the flexible anchor member and the base support of the medical tubing anchor to open the tubing slots so that the length of the medical tubing located between the dressing and the medical tubing anchor is greater than the distance between the access site and the medical tubing anchor, thereby causing the medical tubing to bend in a U shape between the dressing and the medical tubing anchor; and securing the medical tubing in the medical tubing anchor.

In a separate alternative embodiment, the method may further include the steps: placing the adhesive side of the dressing onto an access site of a patient to secure medical tubing, to secure the catheter at the access site, and to protect the access site from contamination; mounting the base support of the tubing anchor onto the skin of the patient on a side of the patient's body where the dressing is located such that the tubing anchor is spacedly disposed from the dressing; squeezing and holding ends of the flexible anchor member and the base support of the medical tubing anchor to open tubing slots in the flexible anchor member; while squeezing and holding ends of the flexible anchor member and the base support, inserting the medical tubing into the medical tubing anchor; after inserting the medical tubing into the medical tubing anchor and while continuing to squeeze and hold ends of the flexible anchor member and the base support, adjusting the medical tubing so that the length of the medical tubing located between the dressing and the medical tubing anchor is greater than the distance between the access site and the medical tubing anchor, thereby causing the medical tubing to bend in a U shape between the dressing and the medical tubing anchor; and securing the medical tubing in the medical tubing anchor.

In yet another embodiment, the method may further include the steps of: placing the adhesive side of the dressing onto an access site of a patient to secure medical tubing, to secure the catheter at the access site, and to protect the access site from contamination; mounting the base support of the tubing anchor onto the skin of the patient on a side of the patient's body where the window dressing is located such that the tubing anchor is spacedly disposed from the dressing; inserting the medical tubing into the medical tubing anchor; adjusting the medical tubing so that the length of the medical tubing located between the dressing and the medical tubing anchor is greater than the distance between the access site and the medical tubing anchor, thereby causing the medical tubing to bend in a U shape between the dressing and the medical tubing anchor; and securing the medical tubing in the medical tubing anchor. The step of adjusting the medical tubing further may include adjusting the medical tubing such that the tubing is slack between the dressing and the tubing anchor.

Further, the step of providing a window dressing may further include providing a window dressing including a closure member having an adhesive side and an opposite non-adhesive side, wherein the closure member is adapted to overlie and close an end of the layer member. The method then may include the steps of: placing the adhesive side of the transparent film layer of the dressing onto an access site of a patient to secure medical tubing, to secure the catheter at the access site, and to protect the access site from contamination; placing the adhesive side of the closure member of the dressing onto an end of the layer member; mounting the base support of the tubing anchor onto the skin of the patient on a side of the patient's body where the window dressing is located such that the tubing anchor is spacedly disposed from the dressing; inserting the medical tubing into the medical tubing anchor; adjusting the medical tubing so that the length of the medical tubing located between the dressing and the medical tubing anchor is greater than the distance between the access site and the medical tubing anchor, thereby causing the medical tubing to bend in a U shape between the dressing and the medical tubing anchor; and securing the medical tubing in the medical tubing anchor.

These and other features and advantages of the invention will be more fully understood from the following detailed description of the invention taken together with the accompanying drawings.

DETAILED DESCRIPTION OF THE INVENTION

Figure 1:
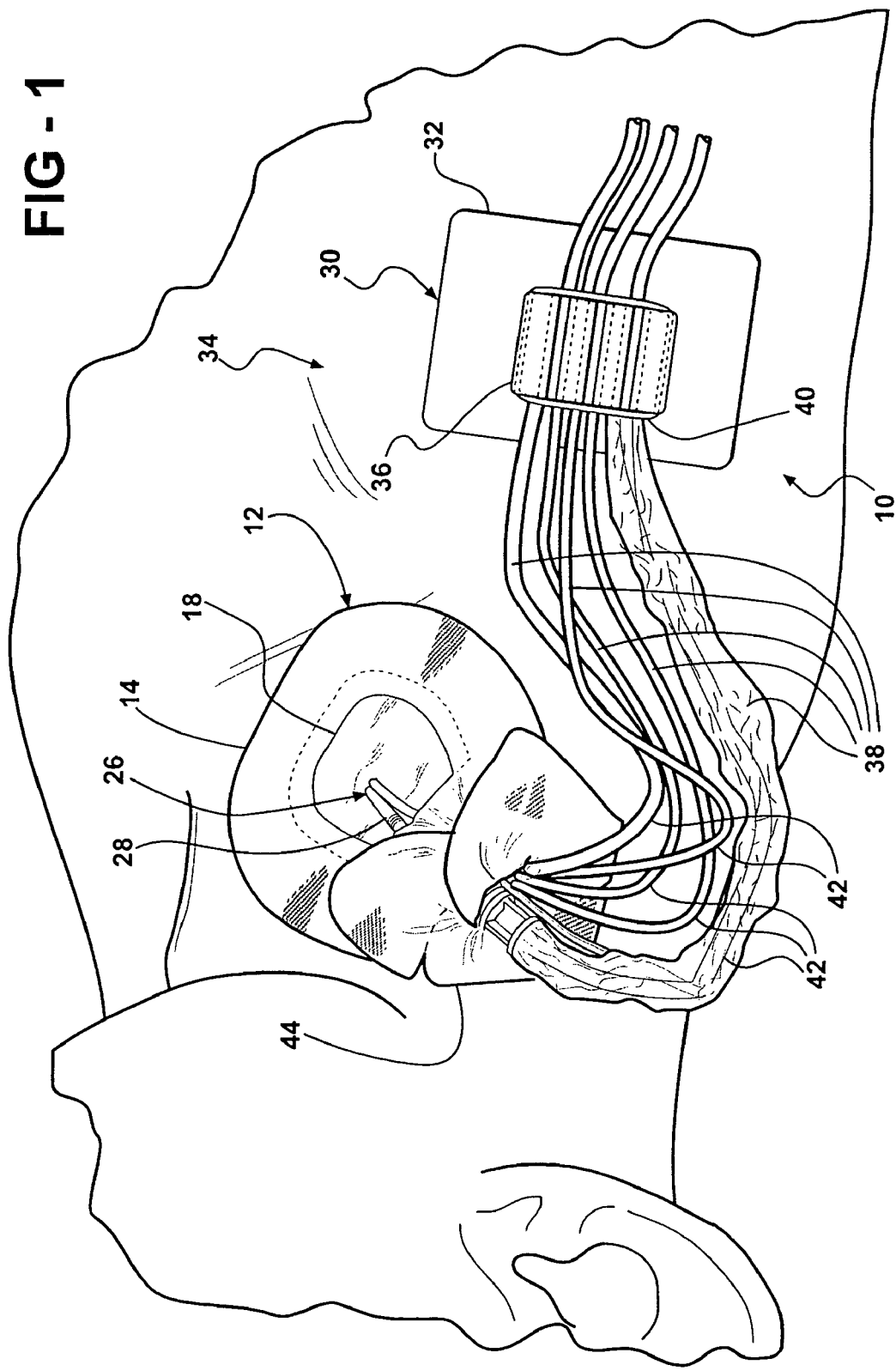
FIG. 1 is an environmental view of an access site dressing, anchoring system in accordance with the present invention.

Referring now to the drawings in detail, numeral 10 generally indicates a system adapted to tend a jugular or subclavian catheter and connecting tubing that prevents inadvertent release of catheter(s) and dressing from a patient's body. The system can accommodate various sizes and combinations of connecting/medical tubing utilized at a jugular or subclavian access site, such as an introducer sheath with a side arm, an introducer sheath with a side arm in combination with a pulmonary artery catheter, and either a single, double, or triple lumen central venous catheter. Moreover, the system can be utilized on either a right-hand side or a left-hand side access site and the system eliminates the forces that cause the dressing to tear away from the skin around the access site.

Figure 2:
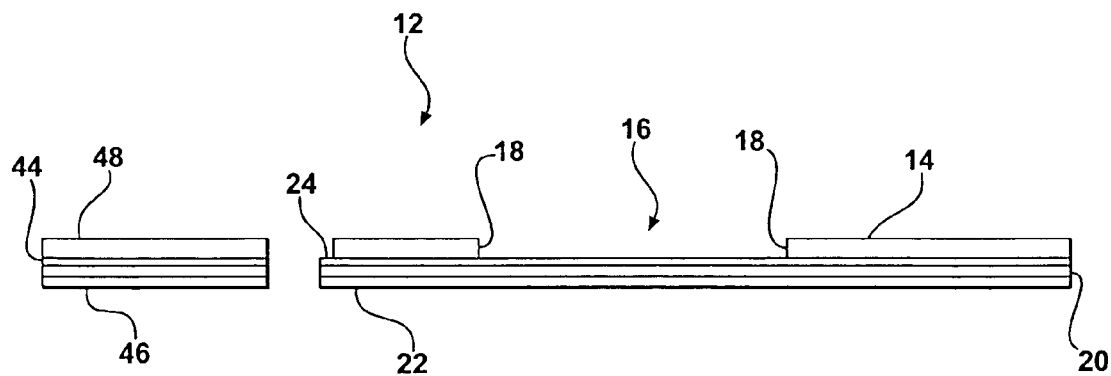
FIG. 2 is a sectional view of a dressing of the system of FIG. 1.
Figure 3:
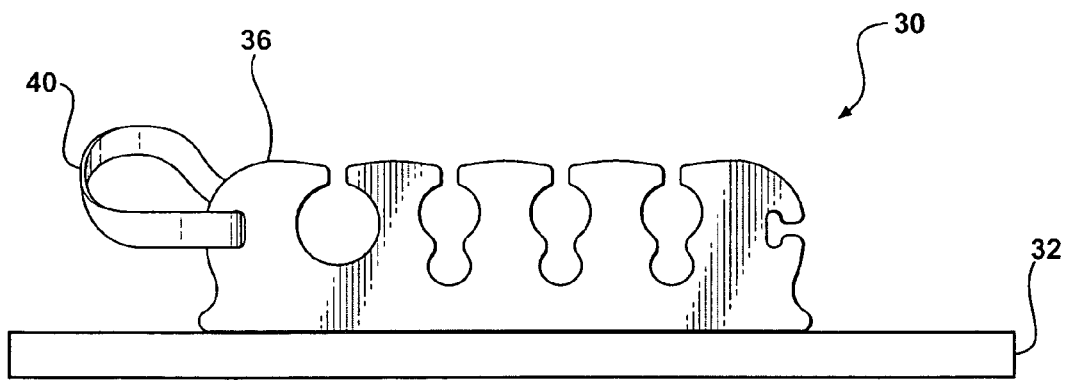
FIG. 3 is a sectional view of a tubing anchor of the system of FIG. 1.

As shown in FIGS. 1 through 3, a preferred system adapted to tend a jugular or subclavian catheter and connecting tubing 10 includes a window dressing 12 of the type including a layer member 14 having an opening 16 therein bounded by an edge 18, and a transparent film layer 20 adhered to a side of the layer member 14 and closing the opening 16. The transparent film layer 20 has an adhesive side 22 and an opposite non-adhesive side 24. The dressing 12 is adapted to protect and cover a catheter access site 26 and at least one catheter 28. The system further includes a medical tubing anchor 30 including a base support 32 adapted to mount to a patient's skin 34 and a flexible anchor member 36 on the base support 32 adapted to receive and support the connecting/medical tubing 38 therein. The medical tubing anchor 30 also includes a keeper 40 on the anchor member 36 for keeping tubing 38 disposed in the anchor member from inadvertent release. The medical tubing anchor 30 is spacedly disposed from the dressing 12. The connecting/medical tubing 38 connects with the catheter 28 and the system 10 allows for movement of the tubing 38 without the tubing exerting a pulling force on the catheter 28, or in turn, the dressing 12.

In one embodiment, the catheter 28 may be chosen from one of a group of single lumen central venous catheters, double lumen central venous catheters, triple lumen central venous catheters, pulmonary artery catheters, or similar. The system 10 may include a plurality of catheters 28. The connecting/medical tubing 38 may be received and supported by the tubing anchor 30 such that at least a portion 42 of the connecting tubing 38 forms a U shape between the dressing 12 and the tubing anchor 30. Alternatively, the connecting/medical tubing 38 may be received and supported by the tubing anchor 30 such that the tubing 38 is slack between the dressing 12 and the tubing anchor 30. The dressing 12 of the system 10 may also include a closure member 44 having an adhesive side 46 and an opposite non-adhesive side 48, wherein the closure member 44 is adapted to overlie and close an end of the layer member 14.

The dressing 12, by way of example, may be a two-piece jugular and subclavian access site window dressing for the protection of a jugular or subclavian catheter access site, which is interchangeably usable on both a right or left access site. This type of dressing includes a anchoring member and a closure member. The anchoring member has an axis that divides the anchoring member into first and second portions. Optionally, the anchoring member axis may be an axis of symmetry. The anchoring member includes a fabric layer having an adhesive side, an opposite non-adhesive side, and an opening therein bounded by an edge, to allow access site viewing through the opening. The anchoring member also includes a transparent film layer that is larger than the opening in all directions, closing the opening in the anchoring member fabric layer. The transparent film layer has an adhesive skin adhering side and an opposite non-adhesive side. The film layer non-adhesive side is adhered onto the adhesive side of the anchoring member fabric layer around the opening such that the transparent film layer extends beyond the edge of the opening.

The closure member of this dressing has an axis that divides the closure member into first and second portions. Optionally, the closure member axis may be an axis of symmetry. The closure member includes a closure member fabric layer that has an adhesive side and an opposite non-adhesive side. The closure member is adapted to overlie and close an end of the anchoring member.

Optionally, the anchoring member fabric layer of this type of dressing further may include symmetrically disposed perforation lines extending from an outer edge of the anchoring member fabric layer towards the anchoring member axis and being generally perpendicular to the anchoring member axis. Each perforation line may terminate before the anchoring member axis at a cross stop cut that is generally parallel to the anchoring member axis. The anchoring member may further include a generally C-shaped pad that is disposed along the edge of the opening, is symmetrically disposed about the anchoring member axis, and is adhered to the adhesive side of the film layer.

The closure member of this type of dressing may include a film layer having an adhesive skin adhering side and an opposite non-adhesive side. The film layer non-adhesive side may be adhered onto the adhesive side of the closure member fabric layer. The closure member also may have symmetrically disposed perforation lines that extend angularly from an outer edge of the closure member towards the closure member axis and meet at a similar point along the closure member axis. The closure member furthermore may include a perforation line extending generally centrally from the outer edge of the closure member at a point located on the closure member axis, run along the closure member axis, and terminate near the center of the closure member at a closure member cross stop cut. The closure member cross stop cut may be generally perpendicular to the closure member axis. The closure member also may include a cut line that extends generally centrally from the outer edge of the closure member at a point located on the closure member axis opposite the point where the center perforation line begins, and ends at the closure member cross stop cut.

The closure member of this type of dressing may also have a pad disposed about the closure member axis near the center of the closure member and adhered to the non-adhesive side of the closure member fabric layer. Alternatively, the pad may extend from one edge of the closure member to another edge of the closure member generally perpendicular to the closure member axis.

The anchoring member and closure member fabric layers of this type of dressing may be made of a tape, cloth, paper, woven, or non-woven material. The transparent film layer may be made of a polyurethane material. The C-shaped pad may be made of a needle punched rayon material having a polyethylene netting side. The C-shaped pad may have absorbent properties. The closure member pad may be made of a resilient or padding-like material such as a polyurethane foam material or a needle punched rayon material.

The medical tubing anchor 30, also by way of example, may be of the type including a base support having an adhesive side and a non-adhesive side. The medical tubing anchor of this type further includes a flexible anchor member that is a generally elongated rectangular solid having two elongated sides, two ends, a base, and a top. The anchor base of the anchor member is mounted on the base support non-adhesive side. The anchor member further has a plurality of stations defined by passageways transversing the anchor member and extending from the anchor member top towards the anchor base. The stations are generally perpendicular to the elongated sides. At least one tube holder having a generally cylindrical cross-section is located along the passageway in each of the stations for receiving medical tubing. The tube holders extend from one elongated side to the other of the elongated sides. A keeper is retainable in the anchor member for keeping medical tubing disposed in the stations from inadvertent release.

In a preferred arrangement, the keeper may be an endless elastic member retainable in a slot located in each of the anchor member ends and the slots may be T-shaped. Alternatively, the keeper may be a band integrally molded with the anchor member at an end of the anchor member. In this embodiment, the keeper further may include a grasp tab integrally connected to the band. The keeper may be retainable in a slot located in the anchor member end opposite the keeper, the slot being configured to receive the grasp tab.

Optionally, the anchor member of this type may be comprised of a material having a hardness that measures between 20 A and 80 A durometer on Shore A scale; preferably 50 A durometer. This material may also be either a polyvinyl chloride material, a polyurethane material, a silicone material, or other non-rigid resin which exhibits friction when rubbed against the resins (typically PVC, PU, or silicone) that IV tubing and catheter tubing are made from. These careful choices of materials and durometer for the anchor member assure the anchor member has enough flexibility to accommodate different sizes of tubing and to assure openability for loading tubing into anchor member tube holders, while also assuring that there is friction between the anchor and the medical tubing to hold the tubing in place and prevent slipping, while at the same time requiring very little tubing OD compression closure force, resulting in no flow restrictions. The base support may be comprised of a foam material chosen of adequate thickness and density to assure that a patient's natural body curvatures are accommodated and to assure patient comfort. The medical tubing anchor may further include a plurality of channels transversing the anchor member along the anchor base. The channels are adaptable to receive adhesive and create retention recesses for the adhesive used to mount the anchor member to the base support, thereby helping to overcome the difficulty of reliably bonding to high plasticizer, low durometer, soft anchor member material resin.

A method for protecting a jugular or subclavian access site 26 of a patient and for securing medical tubing 38 and catheters 28 used during surgery such as open heart or thoracic surgery includes the step of providing a dressing 12 adapted to protect and cover a catheter access site 26 and at least one catheter 28. The dressing 12 includes a layer member 14 having an opening 16 therein bounded by an edge 18, and a transparent film layer 20 adhered to a side of the layer member 14 and closing the opening 16. The transparent film layer 20 has an adhesive side 22 and an opposite non-adhesive side 24. The method further includes the step of providing a medical tubing anchor 30. The medical tubing anchor 30 includes a base support 32 adapted to mount to a patient's skin 34 and a flexible anchor member 36 on the base support 32 adapted to receive and support the connecting/medical tubing 38 therein. The medical tubing anchor 30 also includes a keeper 40 on the anchor member 36 for keeping tubing 38 disposed in the anchor member 36 from inadvertent release.

In one embodiment, the method may further include the steps of: placing the adhesive side 22 of the dressing 12 onto an access site 26 of a patient to secure medical tubing 38, to secure the catheter 28 at the access site 26, and to protect the access site 26 from contamination; inserting the medical tubing 38 into the medical tubing anchor 30 by squeezing and holding ends of the flexible anchor member 36 and the base support 32 to open tubing slots 37 in the flexible anchor member 36; mounting the base support 32 of the tubing anchor 30 onto the skin 34 of the patient on a side of the patient's body where the dressing 12 is located such that the tubing anchor 30 is spacedly disposed from the dressing 12; adjusting the medical tubing 38 by squeezing and holding ends of the flexible anchor member 36 and the base support 32 of the medical tubing anchor 30 to open the tubing slots 37 so that the length of the medical tubing 38 located between the dressing 12 and the medical tubing anchor 30 is greater than the distance between the access site 26 and the medical tubing anchor 30, thereby causing the medical tubing 38 to bend in a U shape between the dressing 12 and the medical tubing anchor 30; and securing the medical tubing 38 in the medical tubing anchor 30.

In an alternative embodiment, the method may further include the steps of: placing the adhesive side 22 of the dressing 12 onto an access site 26 of a patient to secure medical tubing 38, to secure the catheter 28 at the access site 26, and to protect the access site 26 from contamination; mounting the base support 32 of the tubing anchor 30 onto the skin 34 of the patient on a side of the patient's body where the dressing 12 is located such that the tubing anchor 30 is spacedly disposed from the dressing 12; after mounting the base support 32 of the tubing anchor 12 onto the skin 34, inserting the medical tubing 38 into the medical tubing anchor 30 by squeezing and holding ends of the flexible anchor member 36 and the base support 32 to open tubing slots 37 in the flexible anchor member 36; after inserting the medical tubing 38 into the medical tubing anchor 30, adjusting the medical tubing 38 by squeezing and holding ends of the flexible anchor member 36 and the base support 32 of the medical tubing anchor 30 to open the tubing slots 37 so that the length of the medical tubing 38 located between the dressing 12 and the medical tubing anchor 30 is greater than the distance between the access site 26 and the medical tubing anchor 30, thereby causing the medical tubing 38 to bend in a U shape between the dressing 12 and the medical tubing anchor 30; and securing the medical tubing 38 in the medical tubing anchor 30.

In a separate alternative embodiment, the method may further include the steps: placing the adhesive side 22 of the dressing 12 onto an access site 26 of a patient to secure medical tubing 38, to secure the catheter 28 at the access site 26, and to protect the access site 26 from contamination; mounting the base support 32 of the tubing anchor 30 onto the skin 34 of the patient on a side of the patient's body where the dressing 12 is located such that the tubing anchor 30 is spacedly disposed from the dressing 12; squeezing and holding ends of the flexible anchor member 36 and the base support 32 of the medical tubing anchor 30 to open tubing slots 37 in the flexible anchor member 36; while squeezing and holding ends of the flexible anchor member 36 and the base support 32, inserting the medical tubing 38 into the medical tubing anchor 30; after inserting the medical tubing 38 into the medical tubing anchor 30 and while continuing to squeeze and hold ends of the flexible anchor member 36 and the base support 32, adjusting the medical tubing 38 so that the length of the medical tubing 38 located between the dressing 12 and the medical tubing anchor 30 is greater than the distance between the access site 26 and the medical tubing anchor 30, thereby causing the medical tubing 38 to bend in a U shape between the dressing 12 and the medical tubing anchor 30; and securing the medical tubing 38 in the medical tubing anchor 30.

In yet another embodiment, the method may further include the steps of: placing the adhesive side 22 of the dressing 12 onto an access site 26 of a patient to secure medical tubing 38, to secure the catheter 28 at the access site 26, and to protect the access site 26 from contamination; mounting the base support 32 of the tubing anchor 30 onto the skin 34 of the patient on a side of the patient's body where the access site dressing 12 is located such that the tubing anchor 30 is spacedly disposed from the dressing 12; inserting the medical tubing 38 into the medical tubing anchor 30; adjusting the medical tubing 38 so that the length of the medical tubing located between the dressing 12 and the medical tubing anchor 30 is greater than the distance between the access site 26 and the medical tubing anchor 30, thereby causing the medical tubing 38 to bend in a U shape between the dressing 12 and the medical tubing anchor 30; and securing the medical tubing 38 in the medical tubing anchor 30. The step of adjusting the medical tubing 38 further may include adjusting the medical tubing such that the tubing is slack between the dressing 12 and the tubing anchor 30.

Further, the step of providing a dressing 12 may further include providing a dressing 12 including a closure member 44 having an adhesive side 46 and an opposite non-adhesive side 48, wherein the closure member 44 is adapted to overlie and close an end of the layer member 14. The method may then include the steps of: placing the adhesive side 22 of the transparent film layer 20 of the dressing 12 onto an access site 26 of a patient to secure medical tubing 38, to secure the catheter 28 at the access site 26, and to protect the access site 26 from contamination; placing the adhesive side 46 of the closure member 44 of the dressing 12 onto an end of the layer member 14; mounting the base support 32 of the tubing anchor 30 onto the skin 34 of the patient on a side of the patient's body where the access site dressing 12 is located such that the tubing anchor 30 is spacedly disposed from the dressing 12; inserting the medical tubing 38 into the medical tubing anchor 30; adjusting the medical tubing 38 so that the length of the medical tubing 38 located between the dressing 12 and the medical tubing anchor 30 is greater than the distance between the access site 26 and the medical tubing anchor 30, thereby causing the medical tubing to bend in a U shape between the dressing 12 and the medical tubing anchor 30; and securing the medical tubing 38 in the medical tubing anchor 30.

Although the invention has been described by reference to a specific window dressing embodiment, it should be understood that numerous changes may be made within the spirit and scope of the inventive concepts described, including the application of a non-window dressing. Accordingly, it is intended that the invention not be limited to the described embodiment, but that it have the full scope defined by the language of the following claims.

What is claimed is:

1. A method for protecting a jugular or subclavian access site of a patient and for securing medical tubing and catheters used during surgery such as open heart or thoracic surgery, the method comprising the steps of:

providing a dressing adapted to protect and cover a catheter access site and at least one catheter, said dressing comprising:
a layer member having an adhesive side and an opposite non-adhesive side; and
a closure member having an adhesive side and an opposite non-adhesive side, said closure member being adapted to overlie and close an end of said layer member; and providing a medical tubing anchor comprising:
a base support adapted to mount to a patient's skin;
a flexible anchor member on said base support adapted to receive and support said connecting tubing therein; and
a keeper on said anchor member for keeping tubing disposed in said anchor member from inadvertent release;

placing the adhesive side of said dressing onto an access site of a patient to secure medical tubing, to secure the catheter at the access site, and to protect the access site from contamination;

inserting the medical tubing into the medical tubing anchor by squeezing and holding ends of said flexible anchor member and said base support to open tubing slots in said flexible anchor member;

mounting the base support of said tubing anchor onto the skin of the patient on a side of the patient's body where the dressing is located such that the tubing anchor is spacedly disposed from said dressing;

adjusting the medical tubing by squeezing and holding ends of said flexible anchor member and said base support of said medical tubing anchor to open the tubing slots so that the length of the medical tubing located between said dressing and said medical tubing anchor is greater than the distance between the access site and the medical tubing anchor, thereby causing the medical tubing to bend in a U shape between the dressing and the medical tubing anchor; and securing the medical tubing in the medical tubing anchor.

2. A method for protecting a jugular or subclavian access site of a patient and for securing medical tubing and catheters used during surgery such as open heart or thoracic surgery, the method comprising the steps of:

providing a dressing adapted to protect and cover a catheter access site and at least one catheter, said dressing comprising:
a layer member having an adhesive side and an opposite non-adhesive side; and
a closure member having an adhesive side and an opposite non-adhesive side, said closure member being adapted to overlie and close an end of said layer member; and providing a medical tubing anchor comprising:
a base support adapted to mount to a patient's skin;
a flexible anchor member on said base support adapted to receive and support said connecting tubing therein; and
a keeper on said anchor member for keeping tubing disposed in said anchor member from inadvertent release;

placing the adhesive side of said dressing onto an access site of a patient to secure medical tubing, to secure the catheter at the access site, and to protect the access site from contamination;

mounting the base support of said tubing anchor onto the skin of the patient on a side of the patient's body where the dressing is located such that the tubing anchor is spacedly disposed from said dressing;

after mounting the base support of said tubing anchor onto the skin, inserting the medical tubing into the medical tubing anchor by squeezing and holding ends of said flexible anchor member and said base support to open tubing slots in said flexible anchor member;

after inserting the medical tubing into said medical tubing anchor, adjusting the medical tubing by squeezing and holding ends of said flexible anchor member and said base support of said medical tubing anchor to open the tubing slots so that the length of the medical tubing located between said dressing and said medical tubing anchor is greater than the distance between the access site and the medical tubing anchor, thereby causing the medical tubing to bend in a U shape between the dressing and the medical tubing anchor; and securing the medical tubing in the medical tubing anchor.

3. A method for protecting a jugular or subclavian access site of a patient and for securing medical tubing and catheters used during surgery such as open heart or thoracic surgery, the method comprising the steps of:

providing a dressing adapted to protect and cover a catheter access site and at least one catheter, said dressing comprising:
a layer member having an adhesive side and an opposite non-adhesive side; and
a closure member having an adhesive side and an opposite non-adhesive side, said closure member being adapted to overlie and close an end of said layer member; and providing a medical tubing anchor comprising:
a base support adapted to mount to a patient's skin;
a flexible anchor member on said base support adapted to receive and support said connecting tubing therein; and
a keeper on said anchor member for keeping tubing disposed in said anchor member from inadvertent release;

placing the adhesive side of said dressing onto an access site of a patient to secure medical tubing, to secure the catheter at the access site, and to protect the access site from contamination;

mounting the base support of said tubing anchor onto the skin of the patient on a side of the patient's body where the dressing is located such that the tubing anchor is spacedly disposed from said dressing;

squeezing and holding ends of said flexible anchor member and said base support of said medical tubing anchor to open tubing slots in said flexible anchor member;

while squeezing and holding ends of said flexible anchor member and said base support, inserting the medical tubing into the medical tubing anchor;

after inserting the medical tubing into the medical tubing anchor and while continuing to squeeze and hold ends of said flexible anchor member and said base support, adjusting the medical tubing so that the length of the medical tubing located between said dressing and said medical tubing anchor is greater than the distance between the access site and the medical tubing anchor, thereby causing the medical tubing to bend in a U shape between the dressing and the medical tubing anchor; and securing the medical tubing in the medical tubing anchor.

* * * * *